United States Patent
Sproule

[11] 3,938,372
[45] Feb. 17, 1976

[54] VARIABLE ANGLE ULTRASONIC TRANSDUCER FOR SHEAR WAVES

[75] Inventor: Donald Orr Sproule, London, England

[73] Assignee: Videoson Limited, London, England

[22] Filed: Aug. 26, 1974

[21] Appl. No.: 500,692

[30] Foreign Application Priority Data
Sept. 7, 1973  United Kingdom............... 42087/73

[52] U.S. Cl............................ 73/67.8 S; 73/71.5 US
[51] Int. Cl.²........................................ G01N 29/04
[58] Field of Search............... 73/67.5 R, 67.6, 67.7, 73/67.8 R, 67.8 S, 67.9, 71.5 US

[56] References Cited
UNITED STATES PATENTS

| | | | |
|---|---|---|---|
| 2,602,102 | 7/1952 | Webb | 73/71.5 US X |
| 3,257,843 | 6/1966 | Cowan | 73/71.5 US |
| 3,798,961 | 3/1974 | Flambard et al. | 73/71.5 US |

FOREIGN PATENTS OR APPLICATIONS
745,639  2/1956  United Kingdom............ 73/71.5 US

*Primary Examiner*—Richard C. Queisser
*Assistant Examiner*—John P. Beauchamp
*Attorney, Agent, or Firm*—Larson, Taylor and Hinds

[57] ABSTRACT

An ultrasonic probe for generating shear waves in a test piece, having a liquid-filled cell housing a transducer. The cell has a window for application to the test piece and the transducer is pivotable to provide variable angle of wave incidence at the window. An external scale, calibrated in angle of refraction of resultant waves in the test piece, permits of pivoting the transducer for the corresponding angle of incidence by way of a mechanical linkage. For a given wave velocity for a known test piece material (steel and aluminium is chosen) and for a given liquid filling, the linkage geometry is predetermined. Reflected energy within the cell is attenuated by bristle bundles.

10 Claims, 6 Drawing Figures

VARIABLE ANGLE ULTRASONIC TRANSDUCER FOR SHEAR WAVES

This invention relates to probes for ultrasonic waves.

The object of the invention is to provide an improved probe for launching ultrasonic waves in a medium, particularly for non-destructive testing of materials, having particular regard to requirements for launching ultrasonic waves at variable beam angles.

Accordingly, the invention provides an ultrasonic probe, particularly for non-destructive testing of a test piece of known material by generation of ultrasonic shear waves therein, comprising a liquid-retaining cell containing an immersed ultrasonic transducer, the cell having a window in a wall thereof, for placing on a surface of the test piece, the said transducer being mounted for angular movement substantially about a centre located at the cell window, whereby ultrasonic energy is transmitted through the said window to generate shear waves in the said test piece, an attenuating medium being provided within the cell to attenuate reflected ultrasonic waves therein a settable scale and pointer combination, said scale being graduated directly in units related to angle of refraction of said shear waves in the test piece and a mechanical linkage for providing an angular positioning of the transducer according to said scale and pointer setting.

Preferably, the said scale is directly calibrated in angle of refraction units, the geometry of the linkage and pivot points and the wave transmission velocity of the cell-filling medium being fixed and the wave transmission velocity of the test piece material being known.

Conveniently, the window is provided by an aperture in one wall of the said cell which is covered by a liquid retaining flexible membrane, for example rubber sheet.

In a preferred embodiment, the cell filling liquid is water with ethylene glycol additive.

Some problems of non-destructive testing of materials by ultrasonic waves require that the beam angle be adjustable.

This requirement can be satisfied by immersion testing, as described for example in "Non-Destructive Testing", by Hinsley, page 190, by which method both the test piece under test and the probe are immersed in a liquid, usually water. The beam angle can then be readily changed by moving the probe angularly relatively to the test piece. The probe used in such immersion testing can be fitted in a goniometer, so permitting use of a continuously variable range of beam angles.

However, the immersion method of testing requires that the tank be such that multiple echoes, due to the strong reflection at the interface of the test piece and the immersing liquid, arrive at the transducer later than echoes of interest originating inside the test piece itself.

In testing methods using a probe external to the test piece, it is most common to use a series of fixed angle probes for, say 45°, 55°, 65°, 70° and 80°, the angle being determined by a plastics wedge coupling the transducer to the test piece.

Nevertheless, continuously variable angle external probes are known. One such comprises a transducer with a pair of plastics wedges which are rotated oppositely to vary the effective angle between the composite wedge faces. Another such probe comprises a plastics semi-cylinder, with a transducer cemented to the plane face, rotatable within a cylindrical bore in a plastics block. In a third such probe, a plastics block with a quarter-cylindrical convex end-face has an associated transducer cemented to a block with a concave cylindrical face adapted to move over the surface of the plastics block.

Each of these probes is described and illustrated on page 189 of the textbook by Hinsley referred to above.

Each of these probes has its peculiar disadvantages and, commonly, spurious noise due to internal echoes.

In the field of testing by ultransonics, the word "Probe" is sometimes applied to the transducer and the associated insulation and support. In the case of shear wave or other angle-beam probes manually operated, the word is applied to the transducer and also to the associated plastics prism used to produce the desired degree of refraction. In the case of immersion testing, which includes angle-beam testing, the word is applied only to the transducer and the associated housing, the changes in angle in the test piece being carried out by changing the angle of the probe in relation to the surface of the test piece.

The present invention provides, in its preferred form, a composite probe comprising a transducer movably mounted in a liquid-filled cell having a window whereby the liquid-filled cell and the test piece are coupled for the generation of shear waves in the test piece. A continuously variable beam angle is determined by the angular setting of the transducer within the liquid-filled cell. Assuming that the test piece is of steel or aluminum, which materials have a shear wave velocity of $3.2 \times 10^6$ mm/sec, the angular setting of the transducer is obtained by setting an external scale directly calibrated in degrees of angle of refraction of shear waves in the test piece.

In order that the invention may be readily carried into practice, one embodiment of a probe according to the invention will now be described in detail, by way of example, with reference to the accompanying drawings, in which.

Figure 1:
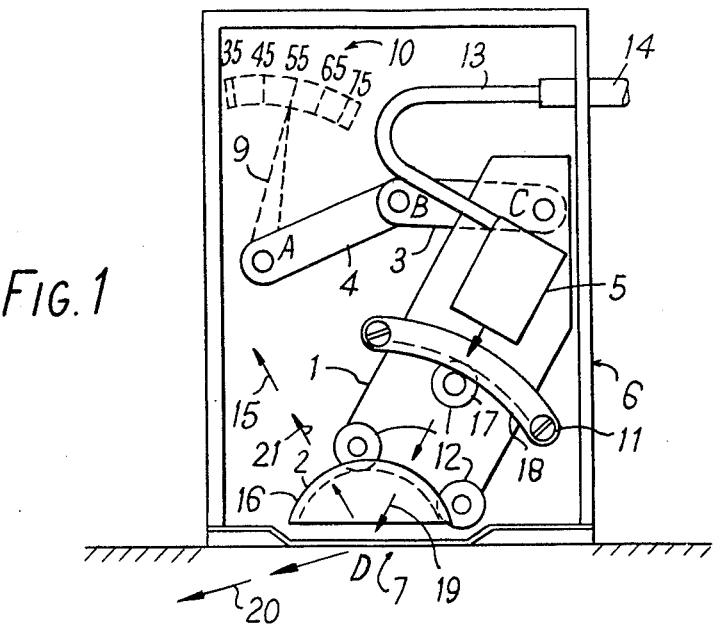
FIG. 1 is a diagram showing the probe in side-elevation, part of the probe being omitted for clarity.

In FIG. 1, there is shown an ultrasonics transducer 5 mounted on a swinging carrying arm 1. The arm 1 is movably mounted in a liquid-filled cell 6, being adapted to swing radially about a point D, which is central of a window 7 in the bottom of the cell 6, as viewed in FIG. 1. To this end, the arm 1 moves around a sector plate 2 centred on the point D. A pair of rollers 12, rotatably attached to the lower end of the arm 1, roll in an arcuate groove 16 in the upper face of the sector plate 2.

A further roller 17, rotatably attached centrally of the arm 1, similarly rolls in a groove 18 formed in the lower face of an arcuate guide member 11.

A link 3, pivotally attached at C, centrally at the top of the arm 1, is pivoted at B to a second link 4. The link 4 has attached thereto a pointer 9, both being pivoted for rotation about a point B, the pointer 9 being external to the cell 6.

When the arm 1 is swung around the point D, the link 3 rotates link 4 about point A and the pointer 9 attached to link 4 is thereby moved over an arcuate scale 10, which is graudated on the external face of the cell 6, to show beam angles between 35° and 75°.

The transducer is supplied with electrical energy by way of a coaxial feeder 13 connected to a coaxial type terminal 14 in the wall of the cell 6.

The cell 6 is liquid-filled, the front cover of the cell 6 being removed in the view of FIG. 1 to show the interior. The transducer 5 is thus immersed in the liquid with which the cell 6 is filled.

In FIG. 1, the cell 6 is shown mounted vertically with the window 7 forming a coupling between the transducer 5 inside the cell 6 and the horizontal face of a test piece of material 8.

The direction of incidence of the ultransonics beam upon the window 7, internally of the cell 6, is represented by the series of arrows 19. The refracted beam, internally of the test piece 8, is shown by the arrows 20. The reflected beam, at the window/test piece interface, is shown by the arrows 21. All series of arrows 19, 20 and 21 terminate, or start, at the point D.

An attenuating medium 15, arranged at the left side of the cell 6 as viewed in FIG. 1, serves to attenuate the reflected energy represented by the arrows 21.

In the embodiment of FIG. 1, the window 7 is of rubber sheet, sealed to the base of the cell 6, thus providing a flexible membrane for contact with the surface of the test piece 8.

Figure 2:
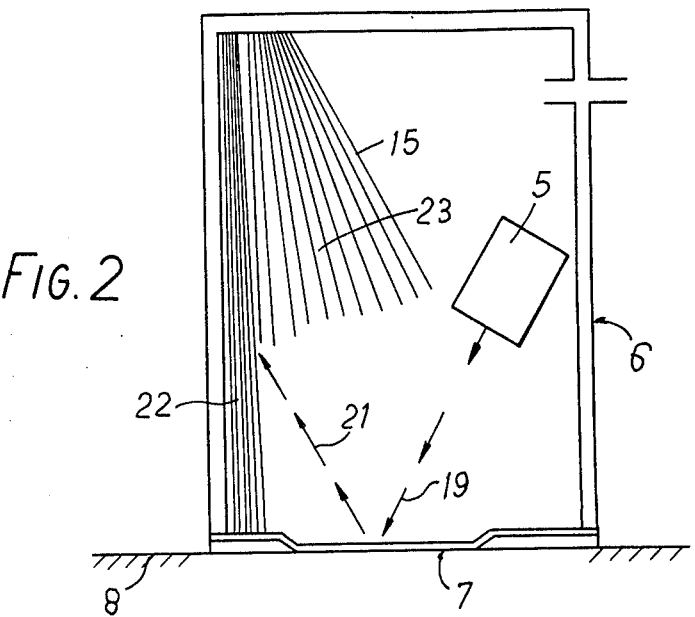
FIG. 2 is a complementary side-elevation view showing particularly the part omitted in the view of FIG. 1.

FIG. 2 is a simplified view of the cell 6 of FIG. 1 with the transducer 5 mounted internally, showing in greater detail the attenuating medium 15.

In the embodiment of FIGS. 1 and 2, the attenuating medium 15 comprises an array of bristles disposed generally as illustrated in FIG. 2. The bristle array 15 comprises a first array of bristles 22, which extend down the left hand side wall of the cell 6 from top to bottom. A second array of bristles 23 is attached near the top wall of the cell 6 and is divergent in the downward direction. The two bristle arrays 22 and 23 are disposed within the cell 6 so that reflected ultrasonic energy passing upwards in the direction 21 enters and is absorbed by the array 22. However, energy reflected from the left end wall of the cell 6 passes through the bristle array 22 a second time and will travel upwardly and leftwardly as viewed in FIG. 2. This energy is attenuated by the bristle array 23. The bristle array 23 thereby prevents further reflection of energy at the top wall of the cell 6.

The effectiveness of the bristle arrays 22 and 23 as an attenuating medium 15 will be explained in greater detail with reference to FIGS. 3, 4 and 5.

A single bristle illuminated by ultrasonic energy in a direction normal to the bristle axis acts in the manner of a line-source, in that it reflects, or reradiates, in specular fashion in the plane containing the bristle axis and scatters in all skew planes.

A bundle of natural animal bristles 60 mm in length, 28 mm wide and 7 mm thick were bonded at their thick ends by an epoxy resin. The bristles of the bundle remained substantially parallel in air but tended to diverge when immersed in water.

Figure 3:
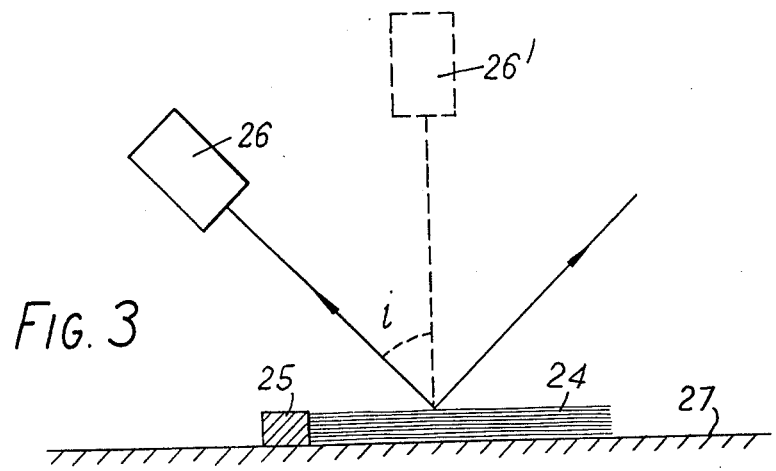
FIGS. 3, 4 and 5 are diagrams showing different dispositions of a bristle bundle referred to in the description of operation of the probe part particularly shown in FIG. 1.

This bristle bundle 24, as shown in FIG. 3, was laid upon the surface of a steel block 27. A transducer 26 was arranged to provide an angle of incidence $i$ of ultrasonic energy upon the upper face of the bristle bundle 24 varying from about 45° to normal incidence at transducer position 26'. An echo derived by normal incidence upon the uncovered face of the steel block 27 gave a reference measurement. Compared with this value, normal echo from the bristle bundle was −40dB. At an incidence of 30° on the bristle bundle face, the echo was reduced to −60dB.

Figure 4:
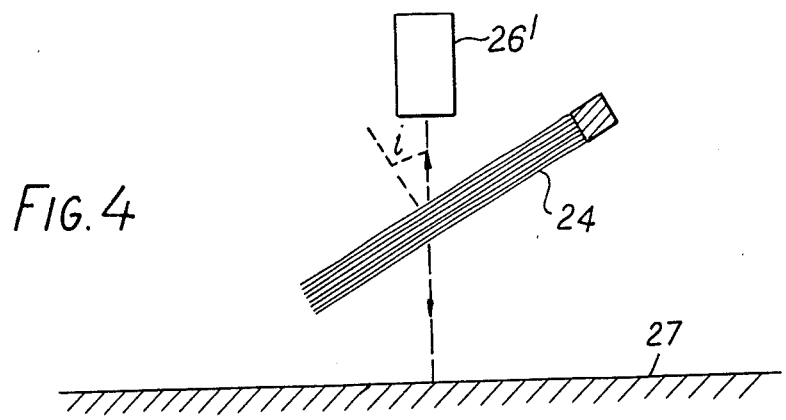

With the transducer retained in position 26' for normal incidence on the face of block 27 and with the bristle bundle 24 rotated about an axis at right angles to the direction of incidence, as shown in FIG. 4, the echo from the block face was −40dB with the bundle axis parallel, diminishing to −60dB with the bundle axis at an angle of 30° and to −70dB at 45°.

Figure 5:
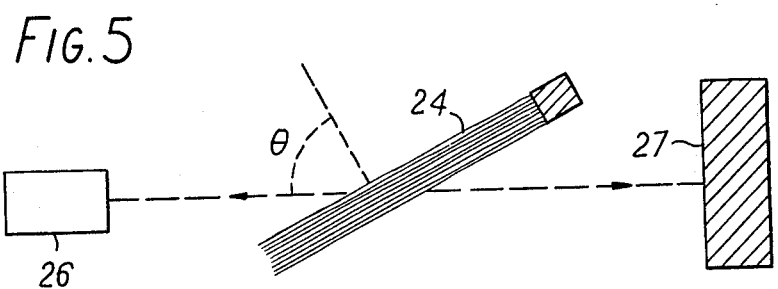

FIG. 5 shows the disposition of the bristle bundle 24 in relation to the transducer 26 and the block 27 to measure reflection from the bristle tips and attenuation of energy passing through the bundle 24, reflected at the surface of block 27 and returning through the bristle bundle 24. Echo from the bristle tips was measured at −60dB to −70dB. The overall attenuation of energy after the double passage through the bundle 24 was −80dB.

In the embodiment of the probe described with reference to FIGS. 1 and 2, the cell 6 is slightly overfilled with liquid so that the membrane window 7 is bowed outwardly, thus providing for better contact with the external surface of a test piece 8. In the views of FIG. 1 and FIG. 2, the membrane window 7 is, of course, flattened against the abutting test piece surface. The liquid thereby displaced from the outwardly bowed membrane window 7 is conveniently accommodated in a second window, not shown, located in any convenient position on the cell body and covered by a stiffer flexible membrane.

To reduce wear on the rubber membrane surface of window 7, the underside of the cell 6 may be provided with hardened steel shoes, not shown in the drawings. Replacement of the rubber membrane of the window 7, when worn, may be facilitated by providing the window with a removable frame, between which frame and the wall of cell 6 the rubber membrane serves as a sealing gasket, retaining the liquid filling the cell 6.

The correct functioning of the probe of FIGS. 1 and 2 provides some restriction on the choice of liquid for filling the cell. The liquid must, of course, serve as an effective couplant between the transducer 5 and the window 7 membrane. The velocity of ultrasonic waves in the medium should not change greatly within the range of ambient temperatures of use. The liquid should be non-corrosive and have a fairly low freezing point.

In the embodiment described, an aqueous filling medium has been found satisfactory and the liquid used comprises water with ethylene glycol additive.

Figure 6:
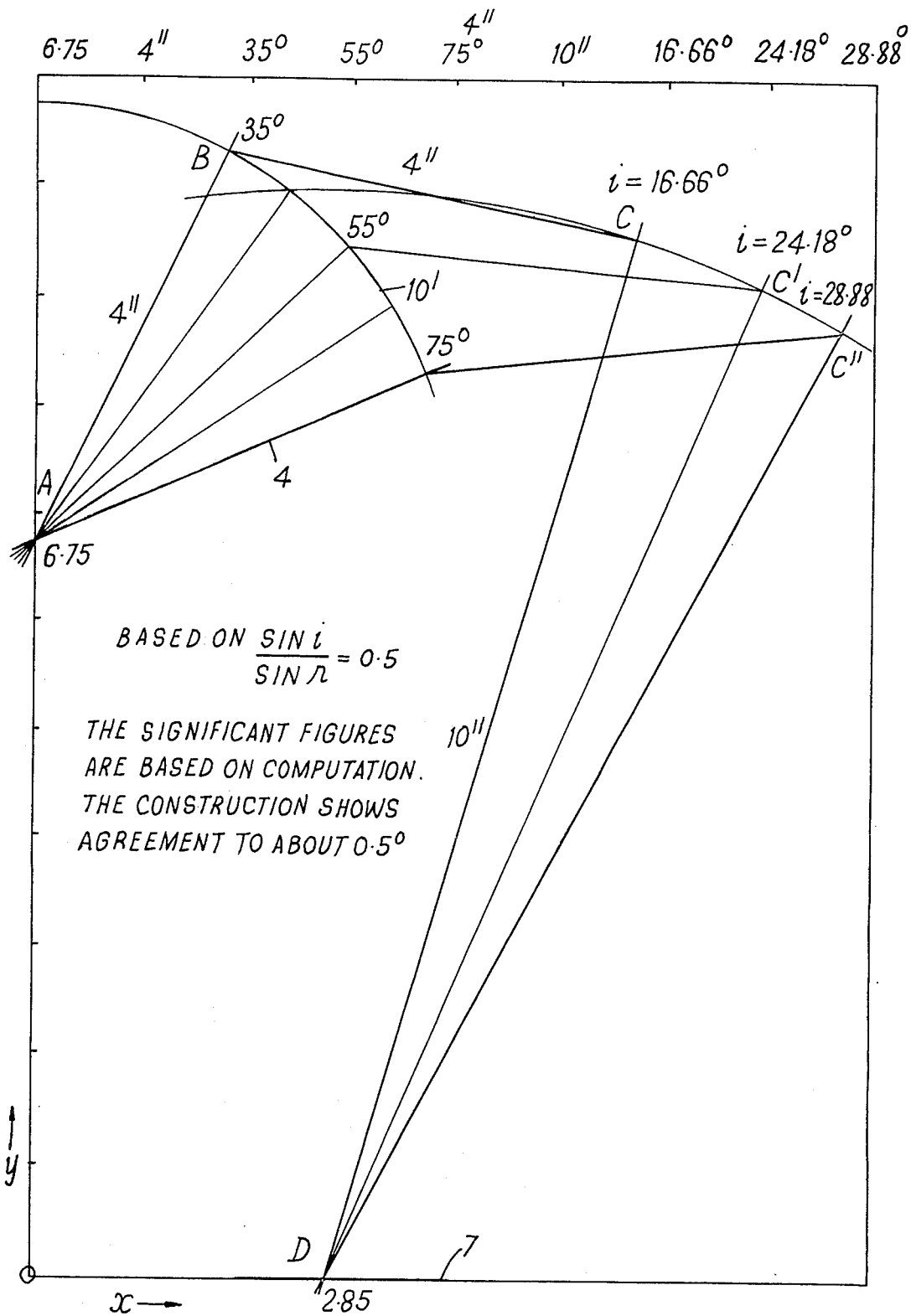
FIG. 6 is a geometrical diagram referred to in the explanation of the design of the probe of FIGS. 1 and 2.

The geometry of the probe of FIGS. 1 and 2 will be seen most clearly from the diagram of FIG. 6, wherein the points indicated by letter in FIG. 1 are similarly represented in FIG. 6 and the surface of window 7 is similarly referenced and the scale 10 is transposed to the equi-angular movement of link 4 at scale 10'.

The dimension D-C is 10 units in length and the dimensions C-B and B-A each 4 units in length.

The axis of rotation of link 4 is $x=0$ and $y=6.75$ on the co-ordinates represented. The axis of rotation of the line CD is $x=2.85$ and $y=0$ on the same co-ordinates.

When link 4, or the attached pointer in FIG. 1, is set to scale reading of 35° for angle of refraction, an angle of incidence of 16.6° is set up. This value is based on the measured velocity of ultrasonic waves in the aqueous filling liquid of cell 6, FIGS. 1 and 2, of $1.6 \times 10^6$ mm/sec. and a shear wave velocity of $3.2 \times 10^6$ mm/sec, whereby $\sin i/\sin r = 0.5$. Thus, it will be seen that the pointer 9 may be set on scale 10 directly to the required angle of refraction and the geometry of the system ensures the angular setting of arm 1, carrying the transducer 5, for that angle of incidence which gives the indicated angle of refraction, for a test piece of steel or aluminium.

Similarly, a pointer setting of 55° gives an angle of incidence of 24.18°, corresponding to the required angle of refraction of 55°.

A pointer setting of 75° gives an angle of incidence of 28.88°, corresponding to the required angle of refraction of 75°.

The units used for the geometry described are arbitrary. Provided that the units are consistent throughout, the geometry can be scaled up or down to give a unit of convenient and practical physical dimensions.

It will be noted that the "angle of refraction" scale 10 is substantially linear. However, the relationship of angular movement of the pointer 9 and the angular movement of the arm 1 is non-linear, as is the relationship between the angle of refraction and the angle of incidence.

The geometry of the linkage is determined by the intended test piece material. For a material other than steel or aluminium, either the scale graduations or the linkage geometry would be changed.

In the use of the device, it is required that the surface of the test piece be at or near the point D and this requirement results from the normal usage described.

The emitting face of the transducer 5 must be spaced sufficiently far from the surface of the test piece 8 to avoid troublesome reflections of the main beam from that surface, and also diffraction effects which lie outside of the main beam. In general, this can be considered as being in the near zone.

In order to keep the complete probe to a size convenient for hand use, and also for use with awkwardly-shaped work pieces, it is necessary to keep the surface-to-test piece distance as small as possible, consistent with the above stated considerations.

For example, an emitting face of 15 mm in diameter should be spaced about 30 mm from the test piece and an additional 30 mm is required to provide clearance for the backing and electrical connections. Thus, the top of the cell 6 will be about 6 cm above the test piece 8.

What we claim is:

1. An ultrasonic probe, particularly for non-destructive testing of a test piece of known material by generation of ultrasonic shear waves therein, comprising a liquid-retaining cell containing an immersed ultrasonic transducer, the cell having a window in a wall thereof, for placing on a surface of the test piece, the said transducer being mounted for angular movement substantially about a centre located at the cell window, whereby ultrasonic energy is transmitted through the said window to generate shear waves in the said test piece, an attenuating medium being provided within the cell to attenuate reflected ultrasonic waves therein, a settable scale and pointer combination, said scale being graduated directly in units related to angle of refraction of said shear waves in the test piece and a mechanical linkage for providing an angular positioning of the transducer according to said scale and pointer setting.

2. An ultrasonic probe as claimed in claim 1, in which the said scale is graduated in degrees of shear angle, the scale and pointer setting is by relative angular movement therebetween and the said linkage provides relatively nonlinear angular movement between the scale and pointer setting and the transducer.

3. An ultrasonic probe as claimed in claim 2, particularly for non-destructive testing of a test piece of material having ultrasonic wave transmission velocity substantially equal to that of steel and aluminium, in which the transducer is carried by a rotatable arm to which the said linkage is attached, the said linkage comprising a rotatable link, of length 4 units, attached to the rotatable member of the scale and pointer combination for rotation therewith, and a second link pivotably attached to the rotatable link and to the rotatable arm carrying the transducer and of length 4 said units, the distance between the latter point of attachment of the said centre of rotation of the transducer being 10 said units of length.

4. An ultrasonic probe as claimed in claim 3, in which the said arm carrying the transducer is mounted by rollers moving around grooved arcuate members to provide said angular movement of the transducer.

5. An ultrasonic probe as claimed in claim 1, in which the said cell window is covered by a liquid-retaining flexible membrane.

6. An ultrasonic probe as claimed in claim 5, in which the said flexible membrane is rubber sheet.

7. An ultrasonic probe as claimed in claim 1, in which the transducer is immersed in an aqueous medium.

8. An ultrasonic probe as claimed in claim 7, in which the said cell is filled with water containing ethylene glycol additive.

9. An ultrasonic probe as claimed in claim 1, in which the attenuating medium comprises at least one array of bristles.

10. An ultrasonic probe as claimed in claim 9, having a first bristle array arranged longitudinally of the side wall of the cell opposite the transducer and a second bristle array arranged at the top of the cell and facing endwise towards the cell window.

* * * * *